(12) United States Patent
Neff et al.

(10) Patent No.: US 7,858,108 B2
(45) Date of Patent: Dec. 28, 2010

(54) ELUTABLE SURFACE COATING

(75) Inventors: Jennifer A. Neff, Rancho Santa Margarita, CA (US); Karin D. Caldwell, Djursholm (SE); Jonas Andersson, Uppsala (SE); Bo Nilsson, Uppsala (SE); Kristina Nilsson-Ekdahl, Uppsala (SE)

(73) Assignee: Richard Nagler, Manhattan Beach, CA (US)

( * ) Notice: Subject to any disclaimer, the term of this patent is extended or adjusted under 35 U.S.C. 154(b) by 1543 days.

(21) Appl. No.: 10/969,541

(22) Filed: Oct. 20, 2004

(65) Prior Publication Data

US 2005/0106208 A1      May 19, 2005

Related U.S. Application Data

(60) Provisional application No. 60/513,057, filed on Oct. 21, 2003.

(51) Int. Cl.
*C08G 63/48* (2006.01)
*C08G 63/91* (2006.01)

(52) U.S. Cl. ............ 424/423; 525/54.1; 525/54.2

(58) Field of Classification Search .............. None
See application file for complete search history.

(56) References Cited

U.S. PATENT DOCUMENTS

| 5,961,923 | A | 10/1999 | Nova et al. |
| 6,087,452 | A | 7/2000 | Stewart et al. |
| 6,224,903 | B1 * | 5/2001 | Martin et al. ............ 424/450 |
| 2004/0142011 | A1 | 7/2004 | Nilsson et al. |
| 2005/0244456 | A1 | 11/2005 | Nilsson et al. |

FOREIGN PATENT DOCUMENTS

| CA | 2503490 | 5/2004 |
| WO | 02077159 A | 10/2002 |

OTHER PUBLICATIONS

"polyethylene oxide" description from Wikipedia.com.*
Neff, J. A. et al.: "A Novel Method for Surface Modification to Promote Cell Attachment to Hydrophobic Substrates," Journal of Biomedical Materials Research, Wiley, New York, NY, US, vol. 40, No. 4, Jun. 15, 1998, pp. 511-519, XP009097674.

* cited by examiner

*Primary Examiner*—Shanon A Foley
(74) *Attorney, Agent, or Firm*—Kirton & McConkie; Evan R. Witt

(57) ABSTRACT

Elutable coatings comprising protein resistant components and bioactive agent on medical devices are disclosed. The elutable coatings comprise labile linkers that can be cleaved under controlled conditions.

19 Claims, 9 Drawing Sheets

ELUTABLE SURFACE COATING

CROSS-REFERENCE TO RELATED APPLICATION

This application claims the benefit of U.S. Provisional Application No. 60/513,057, filed Oct. 21, 2003, which application is incorporated by reference.

BACKGROUND OF THE INVENTION

This invention relates to use of elutable coatings on medical devices for the purpose of delivering compounds.

The systemic administration of drug agents, such as by intravenous means, treats the body as a whole even though the disease to be treated may be localized. Thus, it has become common to treat a variety of medical conditions by introducing an implantable medical device partly or completely into a body cavity within a human or veterinary patient. For example, many treatments of the vascular system entail the introduction of a device such as a stent, catheter, balloon, guide wire, cannula or the like. One of the potential drawbacks to conventional drug delivery techniques with the use of these devices being introduced into and manipulated through the vascular system is that blood vessel walls can be disturbed or injured. Clot formation or thrombosis often results at the injured site, causing stenosis (closure) of the blood vessel.

Other conditions and diseases are also treatable with stents, catheters, cannulae and other devices inserted into the esophagus, trachea, colon, biliary tract, urinary tract and other locations in the body, or with orthopedic devices, implants, or replacements, for example.

Other drawbacks of conventional means of drug delivery using such devices is the difficulty in effectively delivering the bioactive agent over a short term (that is, the initial hours and days after insertion of the device) as well as over a long term (the weeks and months after insertion of the device). Another difficulty with the conventional use of stents for drug delivery purposes is providing precise control over the delivery rate of the desired bioactive agents, drug agents or other bioactive material.

BRIEF SUMMARY OF THE INVENTION

It is desirable to develop devices and methods for reliably delivering suitable amounts of therapeutic agents, drugs or bioactive materials directly into a body portion during or following a medical procedure, so as to treat or prevent such conditions and diseases, for example, to prevent abrupt closure and/or restenosis of a body portion such as a passage, lumen or blood vessel.

In view of the potential drawbacks to conventional drug delivery techniques, there exists a need for a device, method and method of manufacture which enable a controlled localized delivery of active agents, drug agents or bioactive material to target locations within a body.

One embodiment is a class of compounds for coating a medical device for with the formula:

wherein the copolymer comprises one or more hydrophilic domains and at least one hydrophobic domain, labile linker is a linkage that can be cleaved by a controlled factor, and the bioactive agent is any agent such as a pharmaceutical agent or drug or other material that has a therapeutic effect.

Another embodiment is a medical device comprising a class of compounds for coating the medical device with the formula:

wherein the copolymer comprises one or more hydrophilic domains and at least one hydrophobic domain, labile linker is a linkage that can be cleaved by a controlled factor, and the bioactive agent is any agent such as a pharmaceutical agent or drug or other material that has a therapeutic effect.

Another embodiment is a method of coating a medical device with a surface coating comprising a bioactive agent with the formula:

wherein the copolymer comprises one or more hydrophilic domains and at least one hydrophobic domain, labile linker is a linkage that can be cleaved by a controlled factor, and the bioactive agent is any agent such as a pharmaceutical agent or drug or other material that has a therapeutic effect.

Another embodiment is a method of delivering a bioactive compound to a patient with a medical device with a surface coating comprising a bioactive agent with the formula:

wherein the copolymer comprises one or more hydrophilic domains and at least one hydrophobic domain, labile linker is a linkage that can be cleaved by a controlled factor, and the bioactive agent is any agent such as a pharmaceutical agent or drug or other material that has a therapeutic effect.

Other systems, methods, features, and advantages of preferred embodiments will be or become apparent to one with skill in the art upon examination of the following drawings and description. It is intended that all such additional systems, methods, features, and advantages be included within this description, be within the scope of preferred embodiments.

DETAILED DESCRIPTION OF THE INVENTION

Figure 1:
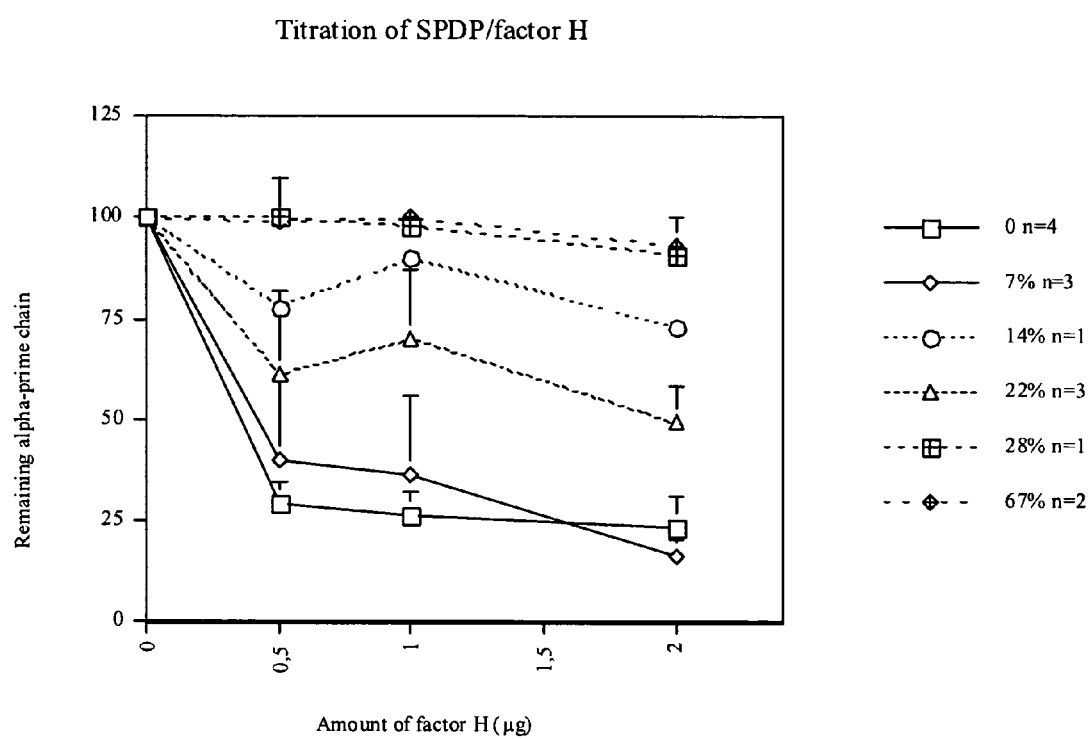
FIG. 1 is a graph showing activity of unmodified Factor H and Factor H derivatized with different concentrations of N-succinimidyl 3-(2-pyridyldithio)propionate (SPDP).
Figure 2:
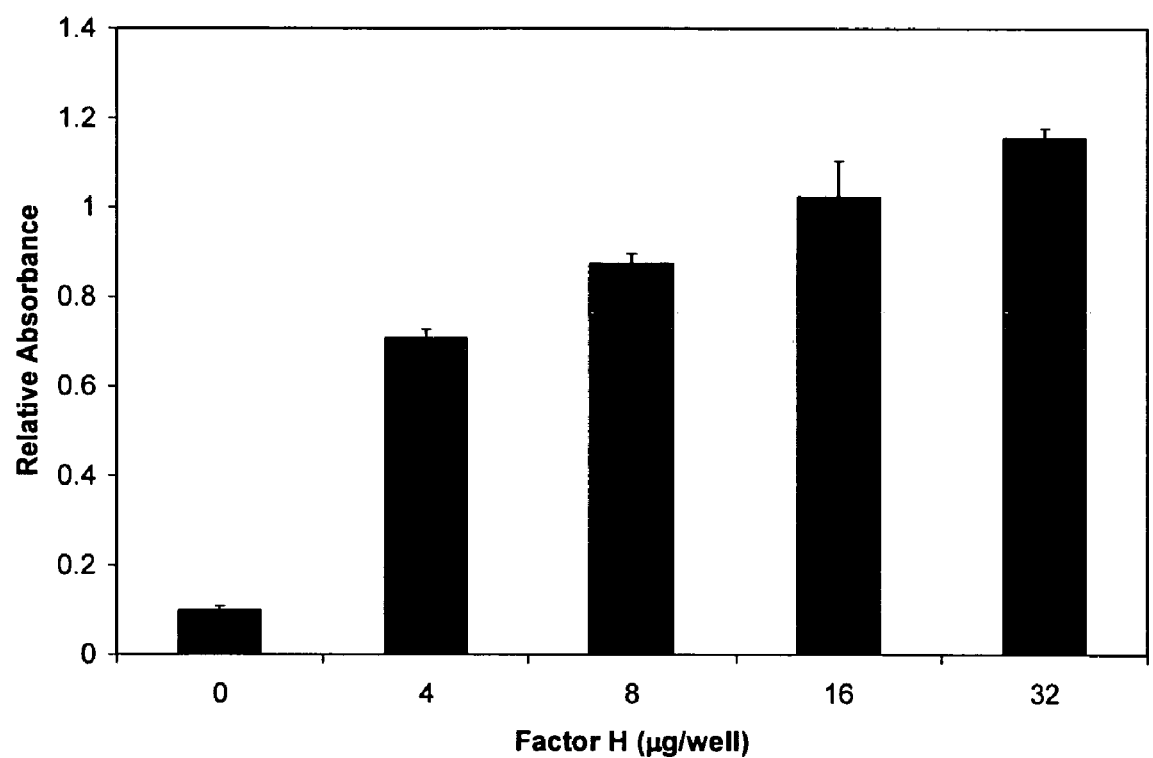
FIG. 2 is a graph showing relative absorbance as a result of Factor H being coupled to polystyrene (PS) in a dose dependent manner using end-group activated polymer (EGAP).
Figure 3A:
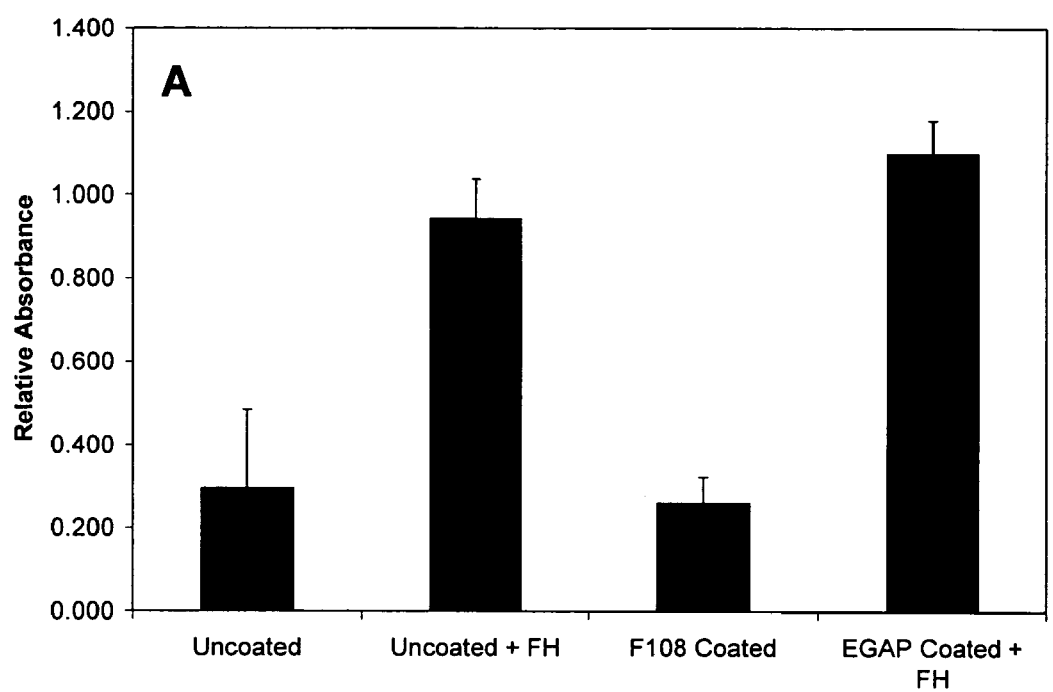
FIG. 3A is a graph showing relative absorbance as a result of Factor H being immobilized on polyether sulfone (PES).
Figure 3B:
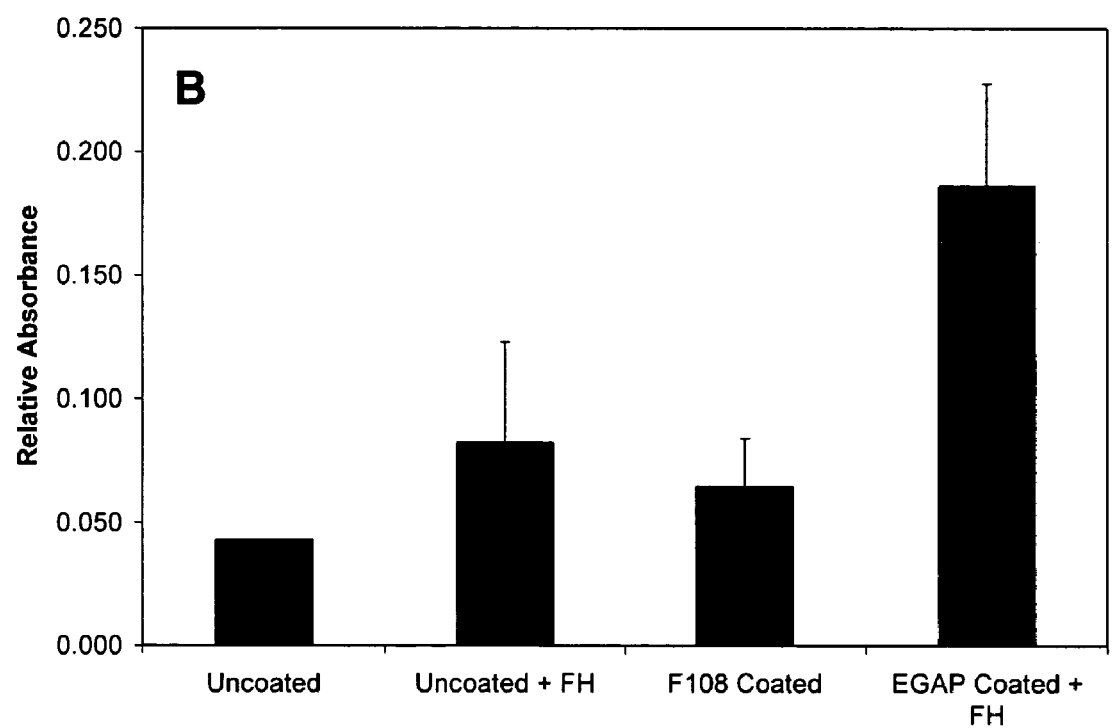
FIG. 3B is a graph showing relative absorbance as a result of Factor H being immobilized on polyurethane (PU).
Figure 3C:
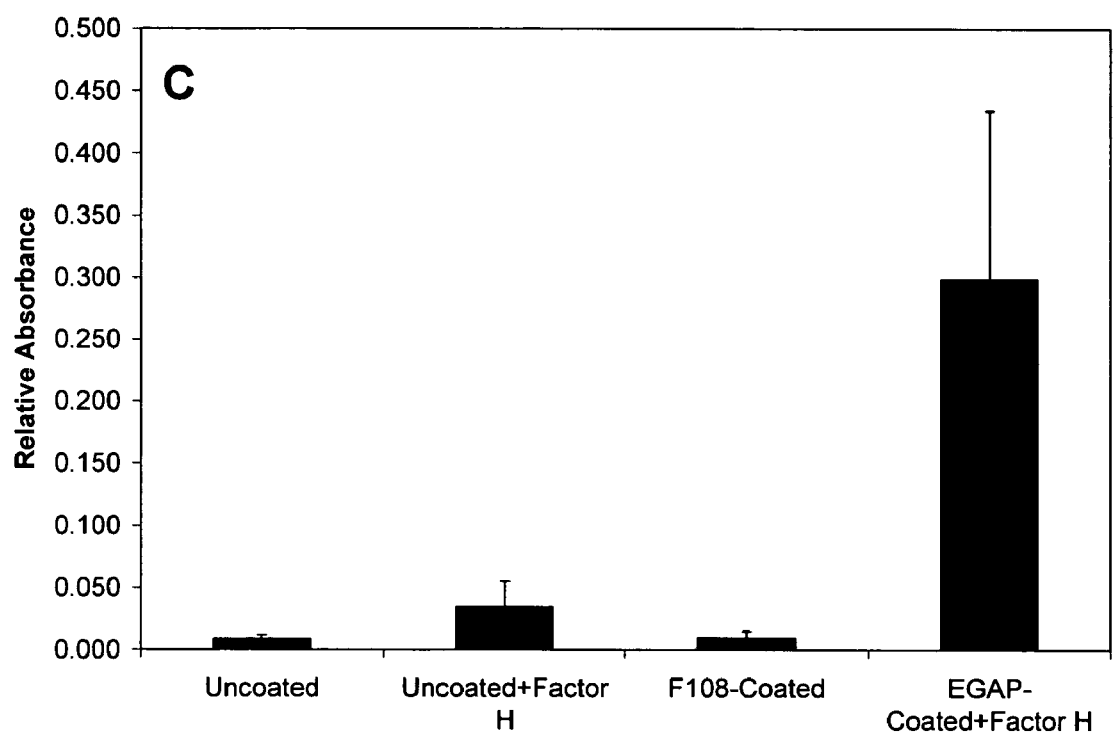
FIG. 3C is a graph showing relative absorbance as a result of Factor H being immobilized on polytetrafluoroethylene (PTFE).
Figure 3D:
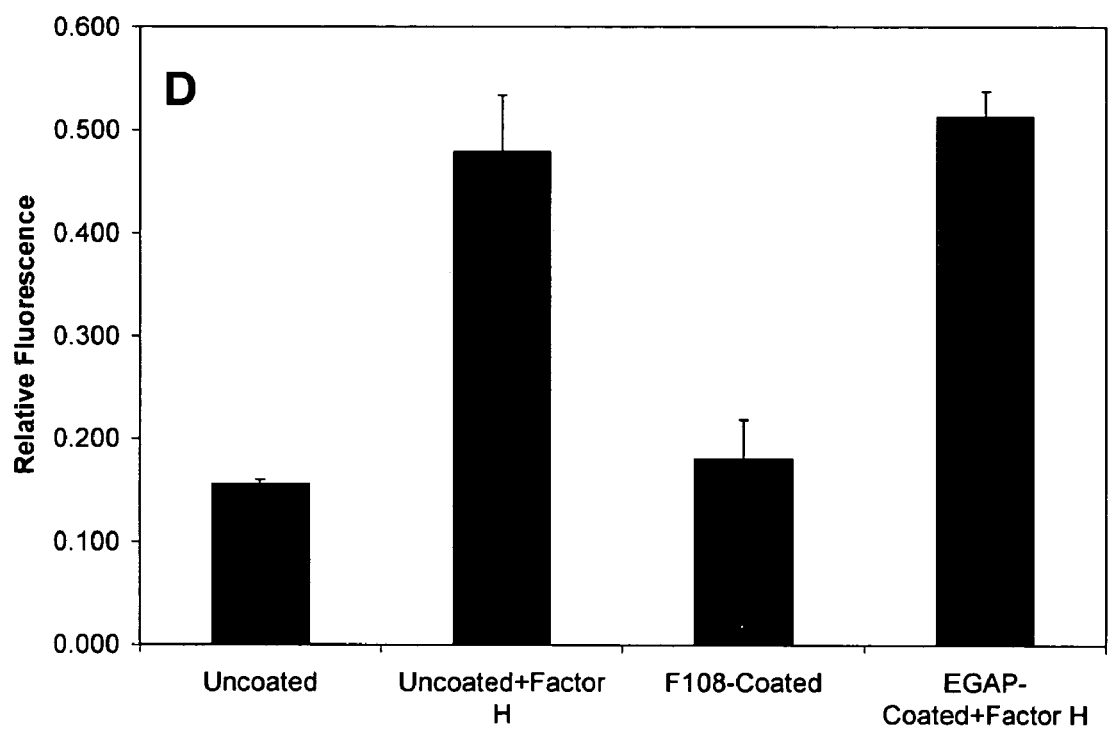
FIG. 3D is a graph showing relative absorbance as a result of Factor H being immobilized on cellulose acetate (CA).
Figure 3E:
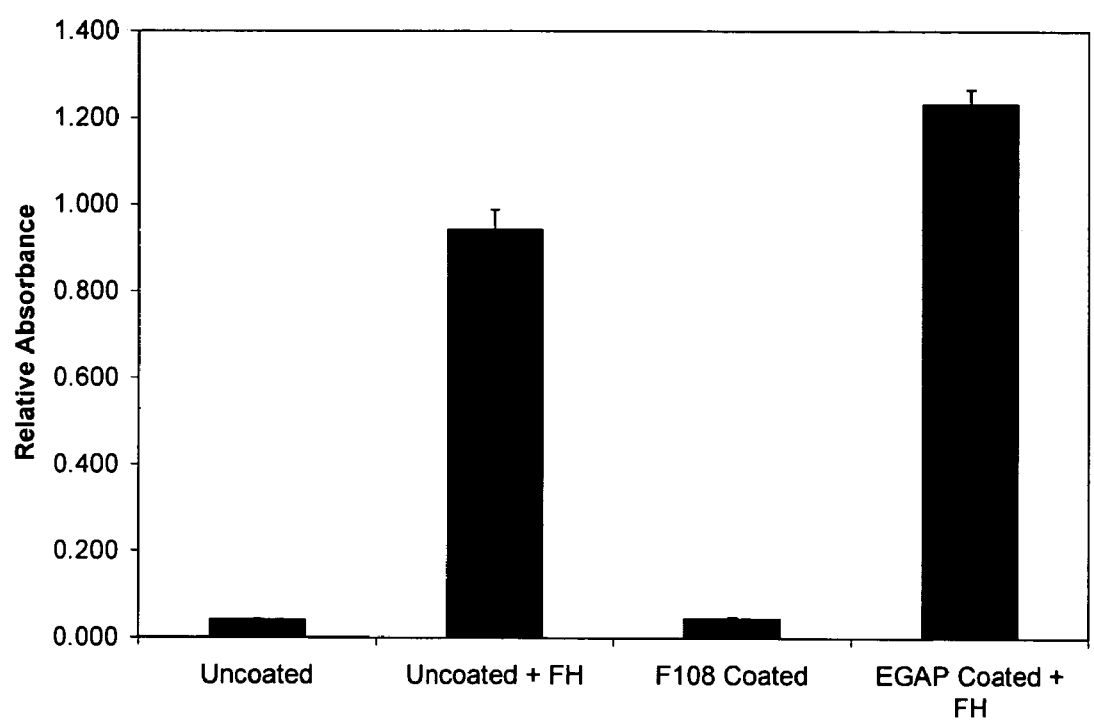
FIG. 3E is a graph showing relative absorbance as a result of Factor H being immobilized on polystyrene (PS).

The preferred embodiments provides a coating comprising a bioactive compound for implantable medical devices and methods for the controlled, localized delivery of a bioactive agent to target locations within a body. The term "controlled localized delivery" as used herein is defined as a characteristic release rate of the bioactive agent at a fixed location.

In an embodiment, a coating is applied to the device comprising a copolymer, a labile linker, and a bioactive agent. Hence, a coating of preferred embodiments provides a copolymer component for adhering to a medical device, a labile linker, and a bioactive agent, as shown below:

wherein the copolymer comprises one or more hydrophilic domains and at least one hydrophobic domain, labile linker is a linkage that can be cleaved by a controlled factor, and the bioactive agent is any agent such as a pharmaceutical agent or drug or other material that has a therapeutic effect. Preferred embodiments include a medical device comprising a class of compounds with the formula:

wherein the copolymer comprises one or more hydrophilic domains and at least one hydrophobic domain, labile linker is a linkage that can be cleaved by a controlled factor, and the bioactive agent is any agent such as a pharmaceutical agent or drug or other material that has a therapeutic effect.

In certain embodiments, the surface to be coated is hydrophobic. Examples of preferred surfaces include, but are not limited to polystyrene (PS), polymethylmethacrylate (PMMA), polyolefins (e.g. polyethylene (PE), polypropylene (PP)), polyvinylchloride (PVC), silicones, polyacrylonitrile (PAN), copolymers of polyacrylonitrile/polyvinal chloride, polysulfone, poly(ether sulfone) (PES), certain polyurethanes, pyrolized materials, and copolymers containing these constituents. Lesser hydrophobic materials and biodegradable materials are also contemplated by the preferred embodiments. These materials include, but are not limited to, polyvinyl acetate (PVAC), cellulose acetate, biodegradable polymers such as (PGA), polylactide (PLA), poly(ϵ-caprolactone, poly(dioxanone) (PDO), trimethylene carbonate, (TMC) polyaminoacids, polyesteramides, polyanhydrides, polyorthoesters and copolymers of these materials.

The coating composition can also be used to coat metals including stainless steel, nitinol, tantalum and cobalt chromium alloys. It is recognized that such materials may require a pretreatment to achieve stable bonding of the coating composition to the substrate. Such pretreatments are well known to those skilled in the art and may involve such processes as silanization or plasma modification. A coating is applied to the material in the form of a multiblock copolymer that contains one or more hydrophilic domains and at least one hydrophobic domain. The hydrophobic domain can be adsorbed to a hydrophobic surface by hydrophobic bonding while the hydrophilic domains can remain mobile in the presence of a fluid phase.

Preferred copolymer units for forming the copolymer coating of preferred embodiments include, but are not limited to, polyethylene oxide (PEO) and polypropylene oxide (PPO), PEO and polybutadiene, PEO and poly(N-acetylethyleneimine), PEO and phenyl boronic acid, PEO and polyurethane, PEO and polymethylmethacrylate (PMMA), and PEO and polydimethyl sulfoxide. In the preceding pairs of copolymer units, preferably, the hydrophilic domain comprises PEO. Copolymers using copolymer units of this type and their application to coating materials to prevent protein adsorption have been described previously [25-30, 31, Han, 1993 #46].

In a certain embodiment, the copolymer comprises pendant or dangling hydrophilic domains, such as poly(ethylene oxide) (PEO) chains. The other domain(s) of the copolymer comprises a hydrophobic domain, such as a poly(propylene oxide) (PPO) chain. Additionally, a linking group (R) is attached to the copolymer on one end adjacent to the hydrophilic domain to form an end-group activated polymer. For example, the end-group activated polymer may be in the form of any arrangement of the PEO and PPO blocks with the general formula:

$$(\text{R-PEO})_a(\text{PPO})_b \quad (1)$$

where a and b are integers, are the same or different and are at least 1, preferably a is between 1 and 6, and b is between 1 and 3, more preferably a is 1 to 2, and b is 1. The polymeric block copolymer has a PEO (—C$_2$H$_4$—O—) content between 10 wt % and 80 wt %, preferably 50 wt % and 80 wt %, more preferably between 70 wt % and 80 wt %.

The PEO chains or blocks are of the general formula:

$$-(-\text{C}_2\text{H}_4-\text{O}-)_u \quad (2)$$

where u is the same or different for different PEO blocks in the molecule. Typically, u is greater than 50, preferably between 50 and 150, more preferably between 80 and 130. The PPO blocks are of the general formula;

$$-(-\text{C}_3\text{H}_6-\text{O}-)_v \quad (3)$$

where v may be the same or different for different PPO blocks in the molecule. Typically, v is greater than 25, preferably between 25 and 75, more preferably between 30 and 60.

The copolymers may be branched structures and include other structures (e.g. bridging structures, or branching structures) and substituents that do not materially affect the ability of the copolymer to adsorb upon and cover a hydrophobic surface. Examples include the following copolymers described in the following paragraphs.

In another embodiment, the end-group activated polymer of preferred embodiments is a derivative of a polymeric triblock copolymer with pendant R groups, as in Formula (4), below. For example, these tri-block copolymers have a hydrophobic center block of polypropylene oxide and hydrophilic end blocks of polyethylene oxide with terminal R groups, and can be represented by the formula:

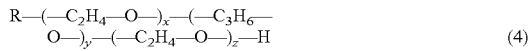
(4)

where y is between 25 and 75, preferably between 30 and 60, and x and z are preferably the same, but may be different, and are between 50 and 150, preferably 80 and 130. Certain types of these polymeric surfactants are commercially referred to as "PLURONIC™" or "POLOXAMERS™", and are available, for example, from BASF.

Another suitable class of polymeric block copolymers is the di-block copolymers where a=1 and b=1, and can be represented by the formula;

R-PEO-PPO—H       (5)

where PEO and PPO are defined above.

Another suitable class of polymeric block copolymers is represented by the commercially available TETRONIC™ surfactants (from BASF), which are represented by the formula:

(6)

As used herein, the terms "PLURONIC" or "PLURONICS" refer to the block copolymers defined in Equation (1), which include the PLURONICS™ tri-block copolymer surfactants, the di-block surfactants, the TETRONIC™ surfactants, as well as other block copolymer surfactants as defined.

In the coatings of preferred embodiments, a labile linker connects the copolymer and the bioactive agent. The labile linker is a linkage which can be selectively cleaved upon exposure to a particular mechanism. Examples of mechanisms include, but are not limited to, hydrolysis, radiation, ultrasound, enzymatic, ionic, diffusion, barrier-mediated diffusion, competitive displacement, and liposomal disruption. The structure of the labile linker depends on the mechanism of cleavage. As disclosed previously, a specific functional group is attached to the free end of a hydrophilic domain to form an end-group activated polymer. The specific functional group (R) eventually becomes a labile linker between the copolymer and bioactive agent in the preferred embodiments.

Protease susceptible linkers are particularly useful because many pathological conditions result in the production or upregulation of certain proteases. By linking a drug or therapeutic molecule to a medical device via a linker that is susceptible to cleavage by such a protease, it is possible to produce a device that releases a drug in response to the on set or changes in an adverse condition. In this way the device acts in a feedback mode and releases drug only when it is needed. It also provides a mechanism for releasing more or less drug in response to a change in the condition. Furthermore, it is possible to vary the amino acid residues that flank the cleavage sites of proteases in order to obtain sequences that will be degraded at lower or higher rates. This enables one to fine tune or control the feedback response of the drug eluting material for a particular condition by controlling the susceptibility of the linker to the environment in which the device will be placed.

As an example, the present invention would be useful for producing coated stents where the coating provides a mechanism for release of an antiinflammitory in response to an increase in the inflammatory state of an artery. Inflammation is known to play a critical role in restenosis after stent implantation. Matrix metalloproteinases (MMP) are an important part of this processes and play a key role in the arterial response to injury. MMP-9 is differentially upregulated as a result of arterial injury and has been found to substantially increase after stent implantation. The present invention would provide a means to link an antiinflammitory drug to the surface of the stent via a linker that is a substrate for MMP-9. After implantation, the antiinflammatory drug would be released if/when the tissue environment signals an unacceptable increase in the level of inflammation.

TABLE 1

Examples of linkers that can be cleaved by different mechanisms.

| Linker | Mechanism of Cleavage |
|---|---|
| Peptides containing either Gly-Ile or Gly-Leu sequence | Protease attack |
| GPQG-IAGQ (SEQ ID NO: 1) | Target of some MMPs |
| VPMS-MRGG (MMP-1 Consensus (SEQ ID NO: 2) | |
| IPVS-LRSG (MMP-2 Consensus) (SEQ ID NO: 3) | |
| RPFS-MIMG (MMP-3 Consensus) (SEQ ID NO: 4) | |
| VPLS-LTMG (MMP-7 Consensus) (SEQ ID NO: 5) | |
| VPLS-LYSG (MMP-9 Consensus) (SEQ ID NO: 6) | |
| IPES-LRAG (MT1-MMP Consensus) (SEQ ID NO: 7) | |
| PAPR-G (SEQ ID NO: 8) | Thrombin |
| GR-G | |
| LDPR-S (SEQ ID NO: 9) | |
| LVPR-GS (SEQ ID NO: 10) | |
| AQCR-KYCP (SEQ ID NO: 11) | Coagulation Factor Xa Coagulation Factor VIIa |
| TKPK-MLPP (SEQ ID NO: 12) | Chymase |
| KPV-SDF (SEQ ID NO: 13) | Cathepsin G Enzyme attack (bond cleavable by complement convertase) |
| Ester bond | Hydrolysis |
| NTA-Ni$^{++}$ - HHHHHH (SEQ ID NO: 14) Metal chelator-metal ion-his tag Protein-protein or protein-peptide interactions that require a divalent ion | Ionic |
| | Competitive displacement |
| | Radiation |

In a preferred embodiment, the specific functional group (R) may contain a member of the reactive group, such as, hydrazine group, maleimide group, thiopyridyl group, tyrosyl residue, vinylsulfone group, iodoacetimide group, disulfide group or any other reactive group that is stable in an aqueous environment and that does not significantly impair the adsorption of the copolymer on the surface.

R can also comprise functional groups capable of forming ionic interactions with proteins, for example a nitrilotriacetic acid (NTA) group, which, when bound to a metal ion forms a strong bond with histidine tagged proteins. NTA modified Pluronics are described in U.S. Pat. No. 6,987,452 to Steward et al., hereby incorporated by reference.

R may also comprise oligonucleotides that can bind to oligonucleotide tagged proteins. Oligonucleotide modified PLURONICS are described in PCT application No. PCT/US02/03341 to Neff et al., hereby incorporated by reference.

In a preferred embodiment, the R group comprises a R'—S—S group where R' is to be displaced for the immobilization of a bioactive agent. Therefore, the labile linker of the preferred embodiments comprises a disulfide bond. The substituent R' is selected from the group consisting of (1) 2-benzothiazolyl, (2) 5-nitro-2-pyridyl, (3) 2-pyridyl, (4) 4-pyridyl, (5) 5-carboxy-2-pyridyl, and (6) the N-oxides of any of (2) to (5). A preferred end group is 2-pyridyl disulfide (PDS).

The reactivity of these groups with proteins and polypeptides is discussed in U.S. Pat. No. 4,149,003 to Carlsson et al. and U.S. Pat. No. 4,711,951 to Axen et al, all of which are hereby incorporated by reference. As mentioned above, end group activated polymers (EGAP)s are generally a class of composition comprising a block copolymer backbone and an activation or reactive group.

Preferred embodiments can include the use of EGAP coatings for affecting delivering bioactive agents. In that respect, the second component of the coating of preferred embodiments can be a bioactive agent that is attached to the material through the activated end groups of the EGAP. The term "bioactive agent" is used herein to mean any agent such as a pharmaceutical agent or drug or other material that has a therapeutic effect. In general terms, a bioactive agent can be a pharmaceutical agent, protein, peptide, proteoglycan, oligonucleotide, protein fragment, protein analog, antibody, carbohydrate or other natural or synthetic molecule. Proteins can be acquired from either natural sources or produced recombinantly. Furthermore, the active domains of these proteins have been identified and recombinantly produced fragments that include these domains may be used. In a certain embodiment, more than one bioactive agent can be immobilized onto one surface with the use of EGAP material. The use of EGAP for protein immobilization has been described previously by Caldwell and others. However, Caldwell and others used EGAP to prepare biologically active surfaces for the purpose of evaluating or promoting specific protein-protein interactions and cell adhesion to surfaces [Neff, 1998 #12; Neff, 1999 #11; Webb, 2000 #8; Li, 1996 #15; Basinska, 1999 #21].

Alternatively, the bioactive agent component of the coating of preferred embodiments can be a therapeutic entity that is capable of removing specific components from a fluid. For example, to remove specific components from blood, the second component can be an antibody.

Bioactive agents that may be delivered using this invention include, but are not limited to, regulators of complement activation, including, Factor H, factor H like protein 1 (FHL-1), factor H related proteins (FHR-3, FHR-4), C4 binding protein (C4bp), complement receptor 1 (CR1), decay-accelerating factor (DAF), membrane cofactor protein (MCP), compstatin, monoclonal antibody inhibitors of complement proteins, oligonucleotide inhibitors of complement proteins, VCP and SPICE; regulators of coagulation or thrombosis, including, antithrombogenic agents, fibinolytic agents, thrombolytic agents, thrombin inhibitors, and antiplatelet agents; vasospasm inhibitors, vasodilators, antihypertensive agents, calcium channel blockers, antimitotics, microtubule inhibitors, actin inhibitors, antiproliferative agents, migration inhibitors, anticancer chemotherapeutic agents, antiinflammitory and immunosuppressive agents, growth factor and cytokine antagonists, growth factors, cytokines, chemotactic agents, gene therapy constructs, antisense oligonucleotides, antioxidants anti microbial agents, bactericidal agents, and anti viral agents.

The modified polymeric surfactant adsorbs with the hydrophobic domain of the copolymer upon the hydrophobic surface and the pendant hydrophilic domain of the copolymer and attached bioactive agent dangling away from the surface into the aqueous surroundings. Using a triblock copolymer as an example, the adsorbed surface can be illustrated by the formula below:

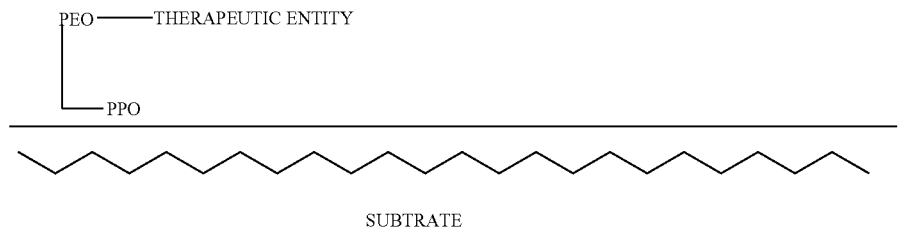

Preferred embodiments can be formed by dipcoating a substrate in a aqueous solution containing EGAP. The EGAP material is applied to the material in a solution of water, buffer, or a combination of water and an organic solvent, such as alcohol. Due to their ampiphilic nature, these copolymers will self assemble on hydrophobic materials from aqueous solutions. The hydrophobic block forms a hydrophobic bond with the material while the hydrophilic blocks remain mobile in the fluid phase. In this way, the hydrophilic chains form a brush like layer at the surface that prevents adsorption of proteins and cells.

When the EGAP material is bonded to the substrate, the material displays an aryl disulfide. A bioactive agent comprising at least one sulfur functional group is incubated with the substrate containing the EGAP material. Through a nucleophilic reaction, the bioactive agent is bonded to the EGAP material by a disulfide bond.

Alternatively, preferred embodiments can be formed by dipcoating a substrate with an EGAP material and subsequently linking a bioactive agent with a heterobifunctional crosslinker. As like the above procedure, the EGAP material is applied to the material in a solution of water, buffer, or a combination of water and an organic solvent, such as alcohol. When the EGAP material is bonded to the substrate, the material displays an activated end group. A bioactive agent is incubated with a heterobifunctional crosslinker; hence, the bioactive agent would display a crosslinkable functional group. The bioactive agent linked to the crosslinker is then incubated with the EGAP material to react with the activated end group. Therefore, the preferable active functional groups on the heterobifunctional crosslinker are sulfhydryl group, to react with a terminal disulfide on the EGAP material, and any functional group that is reactive toward an available functional group on the bioactive agent. Ideally, the crosslinker would not alter the activity of the bioactive agent and could react with the bioactive agent under mild conditions. Such crosslinkers are commercially available from a number of manufacturers. Examples of preferred crosslinkers include N-succinimidyl 3-(2-pyridyldithio)propionate (SPDP), m-maleimidobenzoyl-N-hydroxysuccinimide ester (MBS), and N-succinimidyl S-acetylthioacetate (SATA).

Advantages of preferred embodiments include the use of a non-hazardous coating method, no harsh environmental conditions, no toxic chemicals and no toxic waste products. Preferred embodiments incorporate a simple coating method that is readily incorporated in production process and does not require highly skilled personnel.

The composition of preferred embodiments can be used for any medical device that is in contact with blood. The term "medical device" appearing herein is a device having surfaces that contact human or animal bodily tissue and/or fluids in the course of their operation. The definition includes endoprostheses implanted in blood contact in a human or animal body such as balloon catheters, A/V shunts, vascular grafts, stents, pacemaker leads, pacemakers, heart valves, and the like that are implanted in blood vessels or in the heart. The definition also includes within its scope devices for temporary intravascular use such as catheters, guide wires, and the like which are placed into the blood vessels or the heart for purposes of monitoring or repair. The medical device can be intended for permanent or temporary implantation. Such devices may be delivered by or incorporated into intravascular and other medical catheters.

The compositions of preferred embodiments can be used for any device used for ECC. As stated above, ECC is used in many medical procedures including, but not limited to, cardiopulmonary bypass, plasmapheresis, plateletpheresis, leukopheresis, LDL removal, hemodialysis, ultrafiltration, and hemoperfusion. Extracorporeal devices for use in surgery include blood oxygenators, blood pumps, blood sensors, tubing used to carry blood and the like which contact blood which is then returned to the patient.

The disclosure below is of specific examples setting forth preferred methods. The examples are not intended to limit scope, but rather to exemplify preferred embodiments.

Example 1(A)

Preparation of Substrate with Releasable RCA—Method 1

Pluronic F108 is derivatized to incorporate a terminal PDS group as described by Li et al. This pyridyl disulfide activated Pluronic (EGAP-PDS) is dissolved in phosphate buffer, pH 7.4, 1 mM EDTA (PB) and then mixed with a polypeptide having the sequence CGPQG-IAGQ (SEQ ID NO: 15). The reaction is allowed to proceed for 2 hours at room temperature and is monitored by measuring the release of pyridyl 2-thione spectrophotometrically at 343 nm. The product is purified by dialysis and recovered by lyophilization. Multiple reactions are performed using this approach where the ratio of peptide to EGAP-PDS is varied and the ratio that produces that highest degree of EGAP derivitization is determined.

EGAP modified with the protease susceptible linker (EGAP-PSL) as described above is dissolved in PB. The substrate or device to be coated is incubated with this solution for 30 minutes to overnight. The coated substrate is washed and then incubated with a mixture of EDC and N-hydroxysuccinimide in 4-morpholinoethanesulfonic acid (MES) for 15 minutes at room temperature to convert the carboxy terminus of the peptide to an amine reactive group. The substrate is washed and then incubated with the RCA protein or peptide of interest dissolved in MES for two hours at room temperature. The RCA may be any one of the following: factor H, factor H like protein 1 (FHL-1), factor H related proteins (FHR-3, FHR-4), C4 binding protein (C4bp), complement receptor 1 (CR1), decay-accelerating factor (DAF), membrane cofactor protein (MCP), compstatin, monoclonal antibody inhibitors of complement proteins, VCP or SPICE.

After completion of the reaction, hydroxylamine (10 mM) is added to hydrolyze and deactivate any NHS remaining on the surface.

The amount of RCA on the surface is determined by enzyme immunoassay (EIA).

Example 1(B)

Preparation of Substrate with Releasable RCA—Method 2

A 1% solution of EGAP-PDS in PB is prepared. The substrate to be coated is immersed in this solution for 30 minutes to overnight. The coated substrate is washed with PB and then incubated with a polypeptide having the sequence CGPQG-IAGQ (SEQ ID NO: 15). The reaction is allowed to proceed for 2 hours at room temperature. The substrate is washed with PB.

The modified substrate is washed and then incubated with a mixture of EDC and N-hydroxysuccinimide in 4-morpholinoethanesulfonic acid (MES) for 15 minutes at room temperature to convert the carboxy terminus of the peptide to an amine reactive group. The substrate is washed and then incubated with the RCA protein or peptide of interest dissolved in MES for two hours at room temperature. The RCA may be any one of the following: factor H, factor H like protein 1 (FHL-1), factor H related proteins (FHR-3, FHR-4), C4 binding protein (C4bp), complement receptor 1 (CR1), decay-accelerating factor (DAF), membrane cofactor protein (MCP), compstatin, monoclonal antibody inhibitors of complement proteins, VCP or SPICE. After completion of the reaction, hydroxylamine (10 mM) is added to hydrolyze and deactivate any NHS remaining on the surface.

The amount of RCA on the surface is determined by enzyme immunoassay (EIA).

Example 2(A)

Preparation of Substrate with Releasable RCA—Method 1

Pluronic F108 is derivatized to incorporate a terminal NTA group as described by Ho et al. This pyridyl disulfide activated Pluronic (EGAP-NTA) is dissolved in 25 mM $NiSO_4$ and incubated for 30 minutes. The $Ni^{++}$ charged EGAP-NTA (EGAP-NTA-Ni) is recovered and excess $NiSO_4$ is removed using a size exclusion column. EGAP-NTA-Ni is then mixed with a polypeptide having the sequence HHHHHHGPQG-IAGQ (SEQ ID NO: 16). The reaction is allowed to proceed for 2 hours at room temperature. The product is purified by dialysis and incubated with the substrate or device to be coated for 30 minutes to overnight. The coated substrate is washed and then incubated with a mixture of EDC and N-hydroxysuccinimide in 4-morpholinoethanesulfonic acid (MES) for 15 minutes at room temperature to convert the carboxy terminus of the peptide to an amine reactive group. The substrate is washed and then incubated with the RCA protein or peptide of interest dissolved in MES for two hours at room temperature. The RCA may be any one of the following: factor H, factor H like protein 1 (FHL-1), factor H related proteins (FHR-3, FHR-4), C4 binding protein (C4 bp), complement receptor 1 (CR1), decay-accelerating factor (DAF), membrane cofactor protein (MCP), compstatin, monoclonal antibody inhibitors of complement proteins, VCP or SPICE.

The amount of RCA on the surface is determined by enzyme immunoassay (EIA).

Example 2(B)

Preparation of Substrate with Releasable RCA—Method 2

A 1% solution of EGAP-NTA is prepared in purified water. The substrate to be coated is immersed in this solution for 30 minutes to overnight. After washing the substrate is incubated with 25 mM $NiSO_4$ for 30 minutes at room temperature. The substrate is washed and then incubated with a polypeptide having the sequence HHHHHHGPQG-IAGQ (SEQ ID NO: 16) for 2 hours at room temperature. The modified substrate is washed and then incubated with a mixture of EDC and N-hydroxysuccinimide in 4-morpholinoethanesulfonic acid (MES) for 15 minutes at room temperature to convert the carboxy terminus of the peptide to an amine reactive group. The substrate is washed and then incubated with the RCA protein or peptide of interest dissolved in MES for two hours at room temperature. The RCA may be any one of the following: factor H, factor H like protein 1 (FHL-1), factor H related proteins (FHR-3, FHR-4), C4 binding protein (C4 bp), complement receptor 1 (CR1), decay-accelerating factor (DAF), membrane cofactor protein (MCP), compstatin, monoclonal antibody inhibitors of complement proteins, VCP or SPICE.

The amount of RCA on the surface is determined by enzyme immunoassay (EIA).

Example 3

Characterization of Protease Induced Cleavage of the Suceptible Linker

Polystyrene microsphere samples are coated with the EGAP-PSL construct as described in either Example 1A or Example 1B. The coated microsphere samples are incubated with solutions containing a Matrix Metalloproteinase (MMP-1) immersed.

Example 4

Characterization of Protease Induced Cleavage of the Suceptible Linker and Release of RCA A device or substrate is coated with the EGAP-PSL-RCA construct and described in either Example 1A or Example 1B. The coated substrate is incubated with a solution containing a Matrix Metalloproteinase (MMP-1) immersed.

Example 5

Immobilization of Recombinant RCA-PSL Construct on Substrate Coated with EGAP-PDS A protein or peptide RCA is recombinantly expressed or synthesized, respectively, to contain a protease susceptible linker (PSL) at its N-terminus. The RCA may be any one of the following: factor H, factor H like protein 1 (FHL-1), factor H related proteins (FHR-3, FHR-4), C4 binding protein (C4 bp), complement receptor 1 (CR1), decay-accelerating factor (DAF), membrane cofactor protein (MCP), compstatin, monoclonal antibody inhibitors of complement proteins, VCP or SPICE. The protease susceptible linker will contain a sequence that is a protease target for cleavage and at least one cysteine residue near its N-terminus. An example of such a peptide sequence is CGPQG-IAGQ (SEQ ID NO: 15), which is a target of matrix metalloproteinases. A substrate is coated with EGAP-PDS and then incubated with the RCA-PSL construct in PB for 2 hours at room temperature. The substrate is washed and the amount of RCA bound to the surface is measured by EIA.

Example 6

Immobilization of Recombinant RCA-PSL Construct on Substrate Coated with EGAP-NTA A protein or peptide RCA is recombinantly expressed or synthesized, respectively, to contain a protease susceptible linker (PSL) at its N-terminus. The RCA may be any one of the following: factor H, factor H like protein 1 (FHL-1), factor H related proteins (FHR-3, FHR-4), C4 binding protein (C4 bp), complement receptor 1 (CR1), decay-accelerating factor (DAF), membrane cofactor protein (MCP), compstatin, monoclonal antibody inhibitors of complement proteins, VCP or SPICE. The protease susceptible linker will contain a sequence that is a protease target for cleavage and a polyhistidine tag at its N-terminus. An example of such a peptide sequence is HHHHHHGPQG-IAGQ (SEQ ID NO: 16), which is a MMP target with a six His tag. A substrate is coated with EGAP-NTA and then incubated with 50 mM NiSO4 for 30 minutes at room temperature. The substrate is washed and then incubated with the RCA-PSL construct in PB for 2 hours at room temperature. The substrate is washed and the amount of RCA bound to the surface is measured by EIA.

Example 7

Immobilization of Factor H on Substrate with EGAP

Factor H is coupled to a substrate or device that is coated with EGAP-PDS. Factor H contains numerous cysteine residues, some of which may serve as sites for coupling via the PDS groups [33]. The combination of Factor H and EGAP on the surface of the substrate or device acts to down regulate complement activation.

A device or substrate is coated with Factor H by covering the device surface with a solution containing 0.1 to 4% of EGAP in water or water containing buffer salts. This may be accomplished using a dip coating method, for example. After a coating period of 30 minutes to 24 hours, the substrate is washed using water or buffer. Factor H is diluted into phosphate buffer, pH 7.5, and then added to the coated substrate. After and incubation period of 2-24 hours, the substrate is washed with buffer. The following controls are prepared for comparison: (1) The substrate is coated with unmodified F108 and subsequently incubated with Factor H and washed as indicated above, (2) The substrate is not treated with any initial coating but is incubated with Factor H and washed as indicated above, (3) The substrate is coated with unmodified F108 only, and (4) The substrate is left untreated. The amount of Factor H that is bound to each surface is determined by enzyme immunoassay using a commercially available biotinylated anti-factor H in conjunction with HRP modified streptavidin for detection.

Each substrate is evaluated to determine the ability of the surface bound factor H to inhibit complement activation when it comes into contact with whole blood, plasma or serum. To accomplish this, two types of assays are performed; one being an analysis of the surface to determine what has stuck to it and the other being an analysis of the blood to determine if specific proteins involved in the complement cascade have been activated. The amount of C-3 fragments that are bound to the substrate are determined by enzyme immunoassay (EIA). The amounts of fluid phase C3a, C1s-C1NA, and sC5b-9 complexes that are generated as a result of surface contact between the blood and the substrate are monitored using EIA.

In a previous study, it was found that Factor H could be applied to materials to down regulate complement activation. However, the method used to conjugate factor H to the material was, in of its self, complement activating. Coating a material with EGAP material produces the necessary sites for conjugating Factor H, however, it does not promote compliment activation. To the contrary, it produces a surface that is less biologically active than Polystyrene (PS) and most other materials to which it would be applied for blood contacting devices.

It is anticipated that it will be possible to bind higher amounts of biologically active Factor H to material surfaces than has previously been achieved using alternative methods. A previous study compared the amounts of Factor H bound to surfaces that displayed either pyridyl disulfide groups or sulfhydryl groups. Both surfaces were prepared by reacting a polyamine modified PS with N-succinimidyl 3-(2-pyridyldithio) propionate (SPDP) and the latter was obtained by subsequently treating the surface with dithiothreitol (DTT). It was found that greater amounts of Factor H bound to the material that was modified with SPDP only. In spite of this, the overall biological activity was lower. These results suggest that the conformation of Factor H on the two surfaces differed and that the SPDP modified surface caused a decrease in the biological activity of bound Factor H. PDS groups are more reactive toward free cysteines in factor H and could result in greater coupling efficiency. However, the SPDP modified surface, is also likely to be more hydrophobic and for this reason, it could result in greater amounts of nonspecifically bound proteins as well as a decrease in Factor H activity due to strong interfacial forces between the protein and the material. Using the EGAP approach described herein, it is possible to incorporate PDS groups at the material surface and thereby, achieve high coupling efficiencies without producing a hydrophobic or potentially denaturing surface.

Tethering Factor H to materials using EGAP decreases steric hindrance by incorporating a flexible spacer between the protein and the material. This makes it more accessible for binding to target proteins in blood or plasma.

The EGAP coating produces a highly hydrated brushlike layer at the material surface that effectively buffers the Factor H from the material. This prevents denaturation and preserves the native protein conformation and activity.

The EGAP coating prevents nonspecific protein adsorption. In blood and plasma there are many proteins that when adsorbed onto an artificial material can promote complement activation. For example, when fibrinogen adsorbs onto a material surface, it changes conformation such that it signals for the activation of EGAP prevents this type of interaction and thereby minimizes the risk of immune system activation. When combined with Factor H, the system prevents initial activation and then incorporates a backup, being Factor H that can down regulate any activation that might occur during an ECC procedure.

Example 8

Derivatization of Factor H to Incorporate Sulfhydryl Reactive Group

Factor H was incubated with various concentrations of N-succinimidyl 3-(2-pyridyldithio) propionate (SPDP) ranging from 7 to 67% at room temperature for 1 hour. Unbound SPDP was removed by dialysis. The activities SPDP modified factor H samples were measured and compared to that of unmodified factor H by measuring the ability of factor H to act as a cofactor to factor I. Factor I is another regulator of complement activation that inactivates C3b by cleaving it into inactive C3b (iC3b) and then into C3c and C3dg. This function of factor I is dependent on the presence of active factor H. The activities of the various solutions of modified factor H were thus determined by combining them with C3b and factor I and subsequently measuring the levels of degradation of C3b as follows: Aliquots of 10 µg C3b and 0.6 µg factor I were incubated together with factor H samples in the concentrations of 0.5, 1 and 2, µg for 60 min at 37° C. The reactions were terminated by boiling the samples in reducing electrophoresis sample buffer. The samples were then run on SDS-PAGE. An aliquot containing 10 µg of undigested C3b was added as a control to each gel. The gels were Coomassie stained, scanned and the amount of undigested alfa-prime chain of C3b in each sample was evaluated using NIH-image quant.

The results are shown in FIG. 1. The ratio of SPDP to factor H and the number of samples tested for each data point are given in the legend. The results indicate that Factor H is unaffected after treatment with 7% SPDP, but loses its activity gradually at higher concentrations. At 28% SPDP or higher, a totally inactive factor H is obtained, while concentrations between 25% and 7% yield partial inactivation.

Example 9A

Immobilization of Factor H on Substrate with EGAP and Heterobifunctional Crosslinker Factor H is activated using a heterobifunctional crosslinker and then coupled to a substrate or device that is coated with EGAP. The combination of Factor H and EGAP on the surface of the substrate or device acts to down regulate complement activation.

A device or substrate is coated with Factor H by covering the device surface with a solution containing 0.1 to 4% of EGAP in water or buffer. This may be accomplished using a dip coating method, for example. After a coating period of 30 minutes to 24 hours, the substrate is washed using water or water containing buffer salts. Factor H is activated using a heterobifunctional crosslinker that is reactive towards amine groups, for example, and that incorporates a functional group that can be used to couple directly to the pyridyl disulfide group (PDS) present on EGAP. One such commercially available crosslinker is N-succinimidyl 3-(2-pyridyldithio) propionate (SPDP). The crosslinker incorporates pyridyl disulfide groups on the protein that can be reduced to yield sulfhydryl groups that will react directly with EGAP. Factor H is reacted with SDPD in phosphate buffer, pH 7.5 for 30-60 minutes and then purified using a PD-10 column. The activated protein is treated with 25 mM DTT in acetate buffer, pH 4.5. It is purified using a PD-10 column where it is also exchanged into phosphate buffer, pH 7.5. The product is incubated with the EGAP coated substrate for a period of 2-24 hours followed by washing with buffer. Controls are prepared as described in Example 1. The amount of Factor H that is bound to the surface is determined by enzyme immunoassay using a commercially available biotinylated anti-factor H in conjunction with HRP modified streptavidin for detection.

The modified substrate is evaluated to determine the ability of the surface bound factor H to inhibit complement activation when it comes into contact with whole blood, plasma or serums described in Example 1.

Example 9B

Immobilization of Factor H on Substrate with EGAP and Heterobifunctional Crosslinker Factor H was activated using a heterobifunctional crosslinker, SPDP, and then coupled to an EGAP coated substrate. Using EGAP, it was possible to immobilize factor H in a dose dependant manner.

Substrates were coated with Factor H by covering them with a solution containing 1% of EGAP in water. After a coating period of 24 hours, substrates were washed with water. Control samples were prepared by substituting Pluronic F108 for EGAP using the same procedure. Factor H was activated using a heterobifunctional crosslinker that is reactive towards amine groups and that incorporates a functional group that can be used to couple directly to the pyridyl disulfide group (PDS) present on EGAP. In this example, N-succinimidyl 3-(2-pyridyldithio) propionate (SPDP) was used. Factor H was reacted with SDPD in PBS, pH 7.5 for 30-60 minutes and then purified using a PD-10 column. The crosslinker effectively incorporated pyridyl disulfide groups on the protein. The EGAP coated surface was reduced by incubation with 25 mM DTT for 30 minutes and then washed taking care not to expose the surface to air. Immediately after washing, the substrate was reacted with different concentrations of the SPDP modified factor H for a period of 2-24 hours and finally, washed with buffer. The amount of Factor H that was bound to the surface was determined by enzyme immunoassay using a biotinylated anti-factor H in conjunction with HRP modified streptavidin for detection.

The results are shown in FIG. 2 and indicate that factor H is effectively bound to the surface in a dose dependant manner. Based on the low levels of factor H bound to F108 coated control samples (see FIG. 3(E)), it is clear that the coupling to EGAP-coated surfaces is specifically mediated by functional groups on EGAP.

In a previous study, it was found that Factor H could be applied to materials to down regulate complement activation. However, the method used to conjugate factor H to the material was, in of its self, complement activating. Coating a material with EGAP produces the necessary sites for conjugating Factor H, however, it does not promote compliment activation. To the contrary, it produces a surface that is less biologically active than Polystyrene (PS) and most other materials to which it would be applied for blood contacting devices.

It is anticipated that it will be possible to bind higher amounts of biologically active Factor H to material surfaces using EGAP than has previously been achieved using alternative methods. A previous study compared the amounts of Factor H bound to surfaces that displayed either pyridyl disulfide groups or sulfhydryl groups. Both surfaces were prepared by reacting polyamine modified PS with N-succinimidyl 3-(2-pyridyldithio) propionate (SPDP) and the latter was obtained by subsequently treating the surface with dithiothreitol (DTT). It was found that greater amounts of Factor H bound to the material that was modified with SPDP only. In spite of this, the overall biological activity was lower. These results suggest that the conformation of Factor H on the two surfaces differed and that the SPDP modified surface caused a decrease in the biological activity of bound Factor H. PDS groups are more reactive toward free thiols in factor H and could result in greater coupling efficiency. However, the SPDP modified surface, is also likely to be more hydrophobic and for this reason, it could result in greater amounts of nonspecifically bound proteins as well as a decrease in Factor H activity due to strong interfacial forces between the protein and the material. Using the EGAP approach described herein, it is possible to incorporate functional groups at the material surface with very good reactivity and thereby, achieve high coupling efficiencies without producing a hydrophobic or potentially denaturing surface.

Tethering Factor H to materials using EGAP decreases steric hindrance by incorporating a flexible spacer between the protein and the material. This makes it more accessible for binding to target proteins in blood or plasma. Furthermore, the EGAP coating produces a highly hydrated brush like layer at the material surface that effectively buffers the Factor H from the material. This prevents denaturation and preserves the native protein conformation and activity.

Example 10

Immobilization of Factor H Using EGAP and SATA Crosslinker

Factor H was activated using a heterobifunctional crosslinker, SATA, and then coupled to a substrate or device that was coated with EGAP. The EGAP-factor H coating was effectively applied to various types of materials including polystyrene, polyether sulfone (PES), cellulose acetate (CA), polytetrafluoroethylene (PTFE), silicone, and polyurethane (PU).

Substrates or devices were coated with Factor H by covering the surface with a solution containing 1% EGAP in water. Control samples were prepared by substituting Pluronic F108 for EGAP using the same procedure. Uncoated (UN) samples were also included for comparison. After a coating period of 24 hours, the substrates were washed with buffer. Factor H was activated using a heterobifunctional crosslinker, N-succinimidyl S-Acetylthioacetate (SATA) (Pierce Scientific). The N-hydroxysuccinimide (NHS) ester portion of this crosslinker reacts with amine groups on factor H and incorporates a protected sulfhydryl group that can be used to couple directly to the pyridyl disulfide group present on EGAP. SATA was dissolved in DMSO and then reacted with Factor H in PBS, pH 7.5 for 30-60 minutes. The activated factor H was purified using a PD-10 column. The modified groups on factor H were then deacetylated to remove the protecting group by treatment with hydroxylamine. A final purification on a PD-10 column was performed. EGAP coated substrates were incubated with the modified factor H overnight and then washed with buffer. The amount of Factor H that was bound to the surface was determined by enzyme immunoassay using a biotinylated anti-factor H in conjunction with HRP modified streptavidin for detection. The results are shown in FIG. 3 below and indicate that the EGAP-factor H coating was effectively applied to various types of materials including, polyether ether sulfone (PES), polyurethane (PU), polytetraflouroethylene (PTFE), cellulose acetate (CA), and polystyrene (PS).

Example 11

Reduced Complement Activation on Substrate Coated with EGAP and Factor H. Complement Activation is Measured by Production of C3A Factor H was activated using a heterobifunctional crosslinker and then coupled to an EGAP coated substrate. Coated substrates and controls were incubated with human serum and the level of complement activation was accessed by measuring the amount of C3a generated. EGAP-Factor H coated substrates produced less complement activation compared to controls. Furthermore, both EGAP and F108 coated substrates produced less complement activation than untreated substrates.

A 96 well polystyrene plate was coated with Factor H by adding 300 μL of 1% EGAP in PBS to each well and placing the plate on a shaker at room temperature overnight. After coating, the substrate was washed with PBS. Factor H was reacted with 3.5% w/w SPDP in PBS, pH 7.5 for 1 hour and then purified by dialysis. The EGAP coated substrate was treated with 25 mM DTT for 1 hour. The DTT was removed and the plate was washed with PBS/EDTA pH 6.0 taking care not to expose the substrate to air. After washing, the substrate was immediately reacted with the SPDP activated factor H (100 μg/mL) overnight at 4° C. The factor H solution was removed and the substrate was washed with PBS. The following substrates were used as controls: untreated PS, polystyrene coated with F108 (results not shown), PS coated with EGAP, and PS coated with EGAP followed by incubation with native factor H. All substrates were incubated with human serum for different time periods up to one hour. At the end of each incubation period, EDTA was added to the serum to stop any further complement activation. The amount of C3a in each serum sample was measured by enzyme immunoassay.

Figure 4:
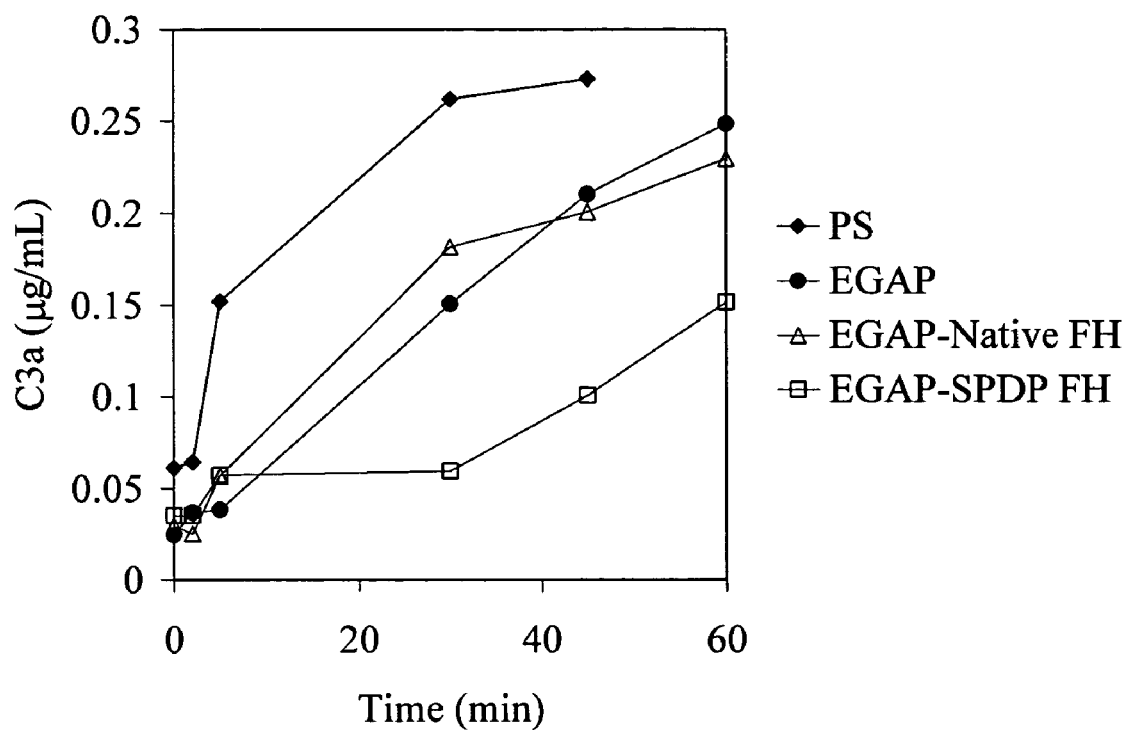
FIG. 4 is a graph showing C3a levels in serum samples that were incubated with untreated PS, polystyrene coated with EGAP, PS coated with EGAP and incubated with native Factor H, or PS coated with EGAP and incubated with SPDP modified Factor H.

The results are shown in FIG. 4 below and indicate that the EGAP-Factor H coating effectively inhibits the generation of C3a compared to controls. Furthermore, the EGAP coating alone reduced the generation of C3a compared to the naked substrate.

Example 12

Immobilization of Factor H on Stainless Steel and Nitinol

Factor H was activated using a heterobifunctional crosslinker, SATA, and then coupled to a stainless steel device that was pretreated followed by coating with EGAP. Factor H was effectively bound to stainless steel via EGAP.

Figure 5:
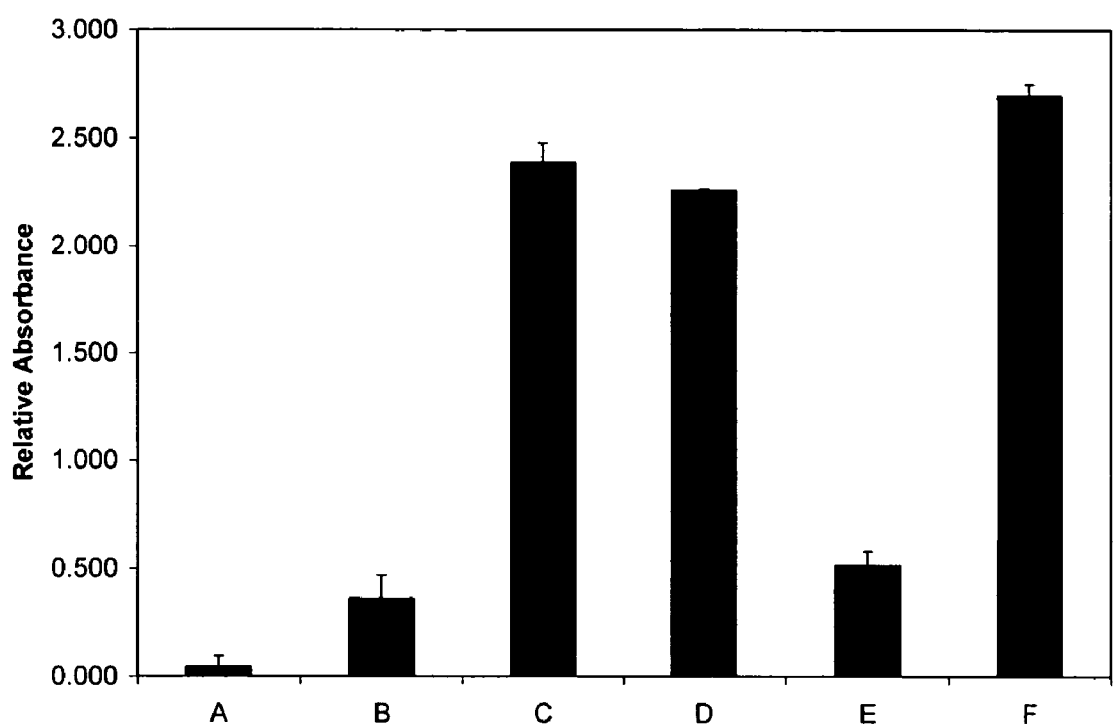
FIG. 5 is a graph showing results of EIA for Factor H bound to various substrates: (A) untreated stainless steel; (B) pretreated stainless steel; (C) stainless steel coated with Factor H; (D) pretreated stainless steel coated with Factor H; (E) pretreated stainless steel coated with F108 followed by Factor H; (F) pretreated stainless steel coated with EGAP followed by Factor H.

Stainless steel and nitinol stent devices were cleaned and/or pretreated followed by coating with EGAP and factor H as described in Example 4. Control samples were prepared by substituting Pluronic F108 for EGAP using the same procedure. Factor H was activated using SATA as described in Example 4. EGAP coated substrates were incubated with the modified factor H overnight and then washed with buffer. The amount of Factor H that was bound to the surface was determined by enzyme immunoassay as described in Example 4. The results for stainless steel are shown in FIG. 5 and indicate that the EGAP-factor H coating was effectively applied to the metal substrate. Furthermore, based on the low amount of H measured on the F108 coated stainless, it is clear that the binding to EGAP coated substrates is specifically mediated by the PDS functional group on EGAP.

Example 13

Immobilization of Factor H on Substrate with EGAP and Unmodified F108

Factor H is coupled to a substrate or device that is coated with a combination of EGAP and unmodified F108. The ratio of EGAP to unmodified F108 is varied in order to vary the number of reactive sites for Factor H coupling and, in turn, vary the surface density of Factor H on the substrate or device. The optimal density of Factor H is determined by measuring the substrate's ability to down regulate complement activation. Although it is likely that the highest density of Factor H possible is optimal for this system, many potentially interesting peptides and synthetic regulators of complement may have some beneficial effects but also possibly some adverse or unknown effects on related blood components including platelets and leukocytes. This EGAP approach potentially provides an optimal system for determining such interactions and how concentrations effect such interactions. Furthermore, the protein, whether produced recombinantly or by purification from natural sources, is the most expensive component of the coating. For this reason, it is beneficial to determine the least amount of protein that can be used to achieve the desired level of performance. This system provides a means to effectively determine this level and subsequently reproduce this level with a high level of confidence.

A series of solutions containing the following ratios of F108 to EGAP are prepared in PBS where the total concentration of surfactant is 1%: (0:100, 5:95, 10:90, 25:75, 50:50, 75:25, 100:0). Substrates are coated with these solutions for a period of 24 hours, followed by washing with PBS. Factor H is diluted into phosphate buffer, pH 7.5, and then added to the coated substrate. After and incubation period of 2-24 hours, the substrate is washed with buffer. The amount of Factor H that is bound to each substrate is determined by enzyme immunoassay using a commercially available biotinylated anti-factor H in conjunction with HRP modified streptavidin for detection.

Each substrate is evaluated to determine the ability of the surface bound factor H to inhibit complement activation when it comes into contact with whole blood, plasma, or serum as described in Example 5.

Example 14

Immobilization of Two or More Therapeutic Entities on Substrate with EGAP

In this example, two or more therapeutic entities are immobilized on a substrate or device using EGAP where each entity affects a different component of the immune or haemostatic system. For example, a regulator of complement might be combined with a regulator of coagulation. EGAP provides a simple method for coimmobilizing two such factors and potentially enables one to control the ratio and densities of the factors, which may very well be critical in the delivery of two or more therapeutic agents from the solid phase.

Two or more types of EGAP are prepared where the end group activation process yields different types of terminal functional groups. These are referred to as EGAP-A and EGAP-B. Two or more therapeutic entities, referred to as TA and TB, are modified to react preferentially with EGAP-A and EGAP-B, respectively. EGAP-A and EGAP-B are combined in a predetermined ratio in PBS where the total concentration of EGAP is 1%. Substrates are coated with these solutions for a period of 24 hours, followed by washing with PBS. If the buffer conditions required for coupling TA to EGAP-A are the same as those required for coupling TB to EGAP-B, then TA and TB are diluted into buffer and added to the coated substrate simultaneously. If different buffer conditions are required, TA and TB are added to the substrate sequentially. Controls are prepared as described in Example 2. The amounts of TA and TB that are bound to each surface are determined by enzyme immunoassay.

Each substrate is evaluated to determine the ability of the combined surface bound TA and TB to inhibit complement activation when the substrate comes into contact with whole blood as described in Example 2.

Example 15

Immobilization of Complement Activation Regulator and Immunocapture Agent on Substrate with EGAP In this example a substrate or device is coated with a regulator of complement activation and an immuno capture agent using EGAP. The purpose of the immunocapture agent is to remove unwanted components from the blood such as autoimmune antibodies, immunoglobulins, immune complexes, tumor antigens, or low-density lipoproteins.

In one variation, the immunocapture agent is immobilized with the regulator of complement activation as described in Example 5. In the other variation one part of the device is coated with EGAP/immunocapture agent and another part of the device is coated with EGAP/regulator of complement activation. In the later variation, the device is coated with EGAP as described in Example 2. The first selected region of the device is then incubated with a solution containing the immunocapture agent by either dip coating or controlled addition of the protein solution to a contained region of the device. The second selected region is then treated similarly with a solution containing the regulator of complement activation.

Example 16

Coating of Therapeutic Entities and Unmodified F108 on Substrate

In this example the device is coated in one region with one or more therapeutic entities as described in any one of the previous examples. The remainder of the device is coated with unmodified F108.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

The references listed below, as well as any other patents or publications referenced elsewhere herein, are all hereby incorporated by reference in their entireties.

REFERENCES

1. Lee, J. H., Kopecek, J., and Andrade, J. D. (1989). Protein-resistant surfaces prepared by PEO-containing block copolymer surfactants. J Biomed Mater Res 23, 351-368.
2. Li, J. T., and Caldwell, K. D. (1996). Plasma protein interactions with Pluronic™-treated colloids. Colloids and Surfaces B: Biointerfaces 7, 9-22.
3. Li, J. T., Carlsson, J., Huang, S.-C., and Caldwell, K. D. (1996). Adsorption of poly(ethylene oxide)-containing block copolymers: a route to protein resistance. In Hydrophillic Polymers. Performance with environmental acceptability, J. E. Glass, ed. (Washington, D.C.: American Chemical Society), pp. 61-78.
4. McPherson, T., Park, K., and Jo, S. (2000). Grafting of biocompatible hydrophilic polymers onto inorganic and metal surfaces. In USPTO, United States Surgical (Norwalk, Conn.): USA.
5. Maechling-Strasser, C., Dejardin, P., Galin, J. C., Schmitt, A., Housse-Ferrari, V., Sebille, B., Mulvihill, J. N., and Cazenave, J. P. (1989). Synthesis and adsorption of a poly (N-acetylethyleneimine)-polyethyleneoxide-poly(N-acetylethyleneimine) triblock-copolymer at a silica/solution interface. Influence of its preadsorption on platelet adhesion and fibrinogen adsorption. J Biomed Mater Res 23, 1395-1410.
6. Winblade, N. D., Nikolic, I. D., Hoffman, A. S., and Hubbell, J. A. (2000). Blocking adhesion to cell and tissue surfaces by the chemisorption of a poly-L-lysine-graft-(poly(ethylene glycol); phenylboronic acid) copolymer. Biomacromolecules 1, 523-533.
7. Winblade, N. D., Schmokel, H., Baumann, M., Hoffman, A. S., and Hubbell, J. A. (2002). Sterically blocking adhesion of cells to biological surfaces with a surface-active copolymer containing poly(ethylene glycol) and phenylboronic acid. J Biomed Mater Res 59, 618-631.
8. Stewart, R. J., Caldwell, K. D., Ho, C. H., and Limberis, L. (2000). Metal-chelating surfactant. In USPTO, University of Utah: USA.
9. Caldwell, K., and Neff, J. A. (2002). End group activated polymers with oligonucleotide ligands. In World Intellectual Property Organization, allvivo, Inc.
10. Axen, R., and Carlsson, J. (1987). Therapeutically active compound and pharmaceutical composition containing the same. In USPTO, Pharmacia Aktiebolag: USA.
11. Carlsson, J., Axen, R., Drevin, H., and Lindgren, G. (1979). Pyridine disulfide compounds. In USPTO, Pharmacia Fine Chemicals AB: USA.
12. Basinska, T., and Caldwell, K. D. (1999). Colloid particles as immunodiagnostics: preparation and FFF characterization. In In Chromatography of Polymers: Hyphenated and Multidimensional Techniques., vol. 731. pp. 163-177, American Chemical Society: Washington D.C.
13. Neff, J. A., Caldwell, K. D., and Tresco, P. A. (1998). A novel method for surface modification to promote cell attachment to hydrophobic substrates. J Biomed Mater Res 40, 511-519.
14. Neff, J. A., Tresco, P. A., and Caldwell, K. D. (1999). Surface modification for controlled studies of cell-ligand interactions. Biomaterials 20, 2377-2393.
15. Webb, K., Caldwell, K., and Tresco, P. A. (2000). Fibronectin immobilized by a novel surface treatment regulates fibroblast attachment and spreading. Crit Rev Biomed Eng 28, 203-208.
16. Li, J. T., Carlsson, J., Lin, J. N., and Caldwell, K. D. (1996). Chemical modification of surface active poly(ethylene oxide)-poly(propylene oxide) triblock copolymers. Bioconjug Chem 7, 592-599.
17. Ripoche, J., Day, A. J., Harris, T. J., and Sim, R. B. (1988). The complete amino acid sequence of human complement factor H. Biochem J 249, 593-602.

The invention claimed is:

1. A compound for coating a medical device with the formula:

wherein the copolymer comprises one or more hydrophilic domains and at least one hydrophobic domain, the labile linker is a linkage that can be selectively cleaved to separate the bioactive agent from the copolymer upon exposure to a cleavage mechanism that is compatible with an in vivo environment in which the medical device is placed, and the bioactive agent is an agent that has a therapeutic effect.

2. The compound according to claim 1, wherein the bioactive agent is a pharmaceutical agent, protein, protein fragment, peptide, oligonucleotide, carbohydrate, proteoglycan, or antibody.

3. The compound according to claim 1, wherein the copolymer comprises polymer units selected from the group consisting of polyethylene oxide (PEO) and polypropylene oxide (PPO), PEO and polybutadiene, PEO and poly(N-acetylethyleneimine), PEO and phenyl boronic acid, PEO and polyurethane, PEO and polymethylmethacrylate (PMMA), and PEO and polydimethyl sulfoxide.

4. The compound according to claim 1, wherein the hydrophilic domain comprises polyethylene oxide.

5. The compound according to claim 1, wherein the hydrophobic domain comprises a polymer unit selected from the group consisting of polypropylene oxide (PPO), polybutadiene, poly(N-acetylethyleneimine), phenyl boronic acid, polyurethane, polymethylmethacrylate (PMMA), and polydimethyl sulfoxide.

6. A medical device comprising a coating, wherein the coating comprises a compound with the formula:

wherein the copolymer comprises one or more hydrophilic domains and at least one hydrophobic domain, the labile linker is a linkage that can be selectively cleaved to separate the bioactive agent from the copolymer upon exposure to a cleavage mechanism that is compatible with an in vivo environment in which the medical device is placed, and the bioactive agent is an agent that has a therapeutic effect.

7. A method of delivering a bioactive compound to an in vivo environment in a mammal comprising
administering to the mammal a medical device comprising a compound with the formula:

wherein the copolymer comprises one or more hydrophilic domains and at least one hydrophobic domain, the labile linker is a linkage that can be selectively cleaved, and the bioactive agent is an agent that has a therapeutic effect; and
cleaving the labile linker by exposure to a cleavage mechanism that is compatible with the in vivo environment in the mammal; thereby
delivering the bioactive compound.

8. The method of claim 7, wherein cleaving the labile linker is performed with a method selected from the group consisting of hydrolysis, radiation, ultrasound, enzymatic, ionic, diffusion, barrier-mediated diffusion, competitive displacement, and liposomal disruption.

9. The compound according to claim 1, wherein the cleavage mechanism functions in response to a change in the in vivo environment in which the medical device is placed.

10. The compound according to claim 1, wherein the labile linker is a protease susceptible linker.

11. The compound according to claim 9, wherein the labile linker comprises a protease cleavage site and amino acid residues flanking the cleavage site that are varied to control the cleavage susceptibility of the cleavage site to the in vivo environment in which the medical device is placed, thereby providing control of the rate at which the bioactive agent is eluted from the medical device.

12. The medical device according to claim 6, wherein the cleavage mechanism functions in response to a change in the in vivo environment in which the medical device is placed.

13. The medical device according to claim 6, wherein the labile linker is a protease susceptible linker.

14. The medical device according to claim 13, wherein the labile linker comprises a protease cleavage site and amino acid residues flanking the cleavage site that are varied to control the cleavage susceptibility of the cleavage site to the in vivo environment in which the medical device is placed, thereby providing control of the rate at which the bioactive agent is eluted from the medical device.

15. The medical device according to claim 6, wherein the cleavage mechanism functions in response to a change in the in vivo environment in which the medical device is placed.

16. The medical device according to claim 15, wherein the labile linker comprises a protease cleavage site and amino acid residues flanking the cleavage site that are varied to control the cleavage susceptibility of the cleavage site to the in vivo environment in which the medical device is placed, thereby providing control of the rate at which the bioactive agent is eluted from the medical device.

17. The method according to claim 7, wherein the cleavage mechanism functions in response to a change in the in vivo environment in which the medical device is placed.

18. The method according to claim 7, wherein the labile linker is a protease susceptible linker.

19. The method according to claim 18, wherein the labile linker comprises a protease cleavage site and amino acid residues flanking the cleavage site that are varied to control the cleavage susceptibility of the cleavage site to the in vivo environment in which the medical device is placed, thereby providing control of the rate at which the bioactive agent is eluted from the medical device.

* * * * *

SEQUENCE LISTING

<160> NUMBER OF SEQ ID NOS: 16

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Gly Pro Gln Gly Ile Ala Gly Gln
1               5

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Val Pro Met Ser Met Arg Gly Gly
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Ile Pro Val Ser Leu Arg Ser Gly
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Arg Pro Phe Ser Met Ile Met Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Val Pro Leu Ser Leu Thr Met Gly
1               5

<210> SEQ ID NO 6
<211> LENGTH: 8
<212> TYPE: PRT
<213> ORGANISM: Artificial Sequence

```
<220> FEATURE:
<223> OTHER INFORMATION: Description of Artificial Sequence: Synthetic
      Peptide

<400> SEQUENCE: 6

Val Pro Leu Ser Leu Tyr Ser Gly
1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Ile Pro Glu Ser Leu Arg Ala Gly
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Pro Ala Pro Arg Gly
1               5

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Leu Asp Pro Arg Ser
1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 10

Leu Val Pro Arg Gly Ser
1               5

<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 11

Ala Gln Cys Arg Lys Tyr Cys Pro
1               5
```

```
<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 12

Thr Lys Pro Lys Met Leu Pro Pro
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 13

Lys Pro Val Ser Asp Phe
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      Peptide
<220> FEATURE:
<221> NAME/KEY: BINDING
<222> LOCATION: (1)..(1)
<223> OTHER INFORMATION: Binds with nitriloacetic acid-Ni++

<400> SEQUENCE: 14

His His His His His His
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 15

Cys Gly Pro Gln Gly Ile Ala Gly Gln
1               5

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 16

His His His His His His Gly Pro Gln Gly Ile Ala Gly Gln
1               5                   10
```